US009216247B2

(12) United States Patent  
Callan et al.

(10) Patent No.: US 9,216,247 B2
(45) Date of Patent: Dec. 22, 2015

(54) BUFFERED COMPOSITIONS FOR DIALYSIS (71) Applicant: Advanced Renal Technologies, Bellevue, WA (US)

(72) Inventors: Robin Callan, Medina, WA (US); Walter A. Van Schalkwijk, Redmond, WA (US); James J. Cole, Arlington, WA (US)

(73) Assignee: Advanced Renal Technologies, Bellevue, WA (US)

( * ) Notice: Subject to any disclaimer, the term of this patent is extended or adjusted under 35 U.S.C. 154(b) by 0 days.

(21) Appl. No.: 14/051,295

(22) Filed: Oct. 10, 2013

(65) Prior Publication Data

US 2014/0034873 A1 Feb. 6, 2014

Related U.S. Application Data (60) Continuation of application No. 13/789,391, filed on Mar. 7, 2013, now abandoned, which is a division of application No. 12/684,546, filed on Jan. 8, 2010, which is a division of application No. 10/606,150, filed on Jun. 24, 2003, now Pat. No. 7,670,491, which is a continuation-in-part of application No. 09/421,622, filed on Oct. 19, 1999, now Pat. No. 6,610,206.

(60) Provisional application No. 60/105,049, filed on Oct. 20, 1998.

(51) Int. Cl.
| | |
|---|---|
| A61K 31/19 | (2006.01) |
| A61K 31/194 | (2006.01) |
| A61K 33/00 | (2006.01) |
| A61K 33/14 | (2006.01) |
| A61K 31/7004 | (2006.01) |
| A61M 1/28 | (2006.01) |
| A61K 33/26 | (2006.01) |
| A61K 45/06 | (2006.01) |
| A61M 1/16 | (2006.01) |

(52) U.S. Cl.
CPC ............... *A61M 1/287* (2013.01); *A61K 31/19* (2013.01); *A61K 31/194* (2013.01); *A61K 31/7004* (2013.01); *A61K 33/00* (2013.01); *A61K 33/14* (2013.01); *A61K 33/26* (2013.01); *A61K 45/06* (2013.01); *A61M 1/1654* (2013.01); *A61M 1/1656* (2013.01)

(58) Field of Classification Search
None
See application file for complete search history.

(56) References Cited

U.S. PATENT DOCUMENTS

| | | | |
|---|---|---|---|
| 3,962,075 A | 6/1976 | Fialkoff et al. | |
| 4,339,433 A | 7/1982 | Kartinos et al. | |
| 4,451,454 A | 5/1984 | Wong | |
| 4,500,309 A | 2/1985 | Diederich et al. | |
| 4,581,141 A | 4/1986 | Ash | |
| 4,661,246 A | 4/1987 | Ash | |
| 4,663,166 A | 5/1987 | Veech | |
| 4,756,838 A | 7/1988 | Veltman | |
| 4,784,495 A | 11/1988 | Jonsson et al. | |
| 4,879,280 A | 11/1989 | Seyffart et al. | |
| 4,886,789 A | 12/1989 | Milner | |
| 4,906,616 A | 3/1990 | Gilchrist et al. | |
| 4,938,873 A | 7/1990 | Rossi | |
| 5,032,615 A | 7/1991 | Ward et al. | |
| 5,108,767 A | 4/1992 | Mulchandani et al. | |
| 5,252,213 A | 10/1993 | Ahmad et al. | |
| 5,447,543 A | 9/1995 | Sadan | |
| 5,474,992 A | 12/1995 | Ogata et al. | |
| 5,589,197 A | 12/1996 | Shockley et al. | |
| 5,591,344 A | 1/1997 | Kenley et al. | |
| 5,616,248 A | 4/1997 | Schal | |
| 5,624,668 A | 4/1997 | Lawrence et al. | |
| 5,645,734 A | 7/1997 | Kenley et al. | |
| 5,651,893 A | 7/1997 | Kenley et al. | |
| 5,658,456 A | 8/1997 | Kenley et al. | |
| 5,674,390 A | 10/1997 | Matthews et al. | |
| 5,674,404 A | 10/1997 | Kenley et al. | |
| 5,690,821 A | 11/1997 | Kenley et al. | |
| 5,698,100 A | 12/1997 | Levin et al. | |
| 5,728,678 A | 3/1998 | Trimbo et al. | |
| 5,762,782 A | 6/1998 | Kenley et al. | |
| 5,780,438 A | 7/1998 | Gilchrist et al. | |
| 5,783,072 A | 7/1998 | Kenley et al. | |
| 5,827,820 A | 10/1998 | duMoulin et al. | |
| 5,851,483 A | 12/1998 | Nicolle et al. | |
| 5,871,477 A * | 2/1999 | Isono et al. | 604/410 |
| 5,906,978 A | 5/1999 | Ash | |

(Continued)

FOREIGN PATENT DOCUMENTS

| | | |
|---|---|---|
| CN | 1328467 A | 12/2001 |
| DE | 41 14 908 A1 | 11/1992 |
| DE | 196 54 746 | 7/1998 |
| EP | 0 022 922 A1 | 1/1981 |
| EP | 0 278 100 A2 | 8/1988 |
| EP | 0 457960 A2 | 11/1991 |
| EP | 0 564 672 | 10/1993 |
| EP | 0 567 452 B1 | 11/1993 |
| EP | 0 821 951 A1 | 2/1998 |
| EP | 0 909 555 A1 | 4/1999 |

(Continued)

OTHER PUBLICATIONS

UC Davis ChemWiki, Chlorides of Period 3 Elements (2014), pp. 1-6.*
ScienceLab.com, MSDS—Calcium Chloride, Anhydrous (2013), pp. 1-5.*
Chemicalland21, Calcium Citrate (2014), p. 1.*

(Continued)

*Primary Examiner* — Abigail Fisher
*Assistant Examiner* — Frank Choi
(74) *Attorney, Agent, or Firm* — Seed IP Law Group PLLC (57) ABSTRACT

Acid concentrates, and dialysate compositions prepared therefrom, contain citric acid and an effective amount of a buffering agent selected from acetate and/or lactate. The buffering agent allows a physiologically acceptable amount of citrate to maintain the desired pH of the dialysate.

8 Claims, 1 Drawing Sheet

(56) References Cited

U.S. PATENT DOCUMENTS

| | | | |
|---|---|---|---|
| 5,945,129 | A | 8/1999 | Knerr et al. |
| 6,019,925 | A | 2/2000 | Diamantoglou et al. |
| 6,077,836 | A | 6/2000 | Milner |
| 6,610,206 | B1 | 8/2003 | Callan et al. |
| 6,673,376 | B1 | 1/2004 | Knerr et al. |
| 6,779,468 | B1 | 8/2004 | Gupta |
| 7,670,491 | B2 | 3/2010 | Callan et al. |
| 7,862,530 | B2 | 1/2011 | Callan et al. |
| 2010/0170849 | A1 | 7/2010 | Callan et al. |
| 2010/0176340 | A1 | 7/2010 | Callan et al. |
| 2011/0172583 | A1 | 7/2011 | Callan et al. |
| 2012/0006748 | A1 | 1/2012 | Callan et al. |
| 2014/0328948 | A1 | 11/2014 | Callan et al. |

FOREIGN PATENT DOCUMENTS

| | | |
|---|---|---|
| EP | 1 721 606 B1 | 10/1999 |
| EP | 0 821951 A1 | 2/2000 |
| EP | 1 059 083 | 12/2000 |
| EP | 1 124567 B2 | 6/2011 |
| EP | 2 452 685 A1 | 5/2012 |
| JP | 6-335528 A | 12/1994 |
| JP | 6335527 | 12/1994 |
| JP | 8-92070 A | 4/1996 |
| JP | 10-87478 A | 4/1998 |
| WO | WO 92/11046 A1 | 7/1992 |
| WO | WO 93/24108 A1 | 12/1993 |
| WO | WO 96/01118 A1 | 1/1996 |
| WO | WO 97/48365 A1 | 12/1997 |
| WO | WO 98/06482 | 2/1998 |
| WO | WO 98/29151 A1 | 7/1998 |
| WO | WO 98/29434 | 7/1998 |
| WO | WO 99/07419 | 2/1999 |
| WO | WO 00/23086 | 4/2000 |
| WO | WO 01/00204 A1 | 1/2001 |
| WO | WO 01/21233 A1 | 3/2001 |
| WO | WO2005/002599 A1 | 1/2005 |

OTHER PUBLICATIONS

Pharmco-Aaper, Product Specification Sheet, Magnesium Citrate Tribasic, Anhydrous (2005).*

S.A. Citrique Beige N.V., Product Data Sheet, Trisodium Citrate Dihydrate (2009), pp. 1-3.*

International Preliminary Examination Report for International Application No. PCT/US99/24583 mailed Feb. 5, 2001, 7 pages.

Ahmad et al., "Effect of the Normalization of Acid-Base Balance on Postdialysis Plasma Bicarbonate," *Trans. Am. Soc. Artif. Intern. Organs* 26: 318-321, 1980.

Ahmad et al., "Increased Dialyzer Efficiency Using a Dialysate Containing Citric Acid in Place of Acetic Acid," *J. Am. Soc. Nephrol.* 10: 188A, Abstract A0961, 1999.

Apsner et al., "A Simple Method for Citrate Anticoagulation (CA) during High Flux Dialysis: Experience with 760 Dialyses in 34 Patients," *J. Am. Soc. Nephrol.* 10: 188A, Abstract A0962, 1999.

Brady and Hasbargen, "Correction of Metabolic Acidosis and Its Effect on Albumin in Chronic Hemodialysis Patients," *Am. J. Kid. Dis.* 31(1): 35-40, Jan. 1998.

Callan et al., SIPO English Abstract for CN 1328467 published Dec. 26, 2001.

Caruana and Keep, "Anticoagulation", in John T. Daugirdas, M.D. and Todd S. Ing, M.D. (eds.), *Handbook of Dialysis*, Little, Brown and Company, 1994, pp. 121-135.

Caruana et al., "Heparin free dialysis: Comparative data and results in high risk patients," *Kidney International* 31: 1351-1355, 1987.

Casati et al., "Hemodialysis without anticoagulants in patients with high bleeding risk," *International Journal of Artificial Organs* 5(4): 233-236, 1982.

Citrasate® Additive Chart, http://www.dialmedsupply.com/citrasate/PDF/Citrasate_Additives.pdf, download date Nov. 24, 2009.

Daugirdas, "Second Generation Logarithmic Estimates of Single-Pool Variable Volume Kt/V: An Analysis of Error," *J. Am. Soc. Nephrol.* 4: 1205-1213, 1993.

Derwent World Patent Index Database No. 199508, Acc. No. 1995-056931, Abstract of JP 06 335527, Dec. 6, 1994.

Derwent World Patent Index Database No. 199624, Acc. No. 1996-235949, Abstract of JP-A-8 092 070, Apr. 9, 1996.

Derwent World Patent Index Database No. 199824, Acc. No. 1998-267011, Abstract of JP 10 087478, Apr. 7, 1998.

Drukker et al., *Replacement of Renal Function by Dialysis*, Fourth Edition, Kluwer Academic Publishers, Dordrecht, The Netherlands, 1996, p. 345.

Dzik and Kirkley, "Citrate Toxicity During Massive Blood Transfusion," *Transfusion Medicine Reviews* 2(2): 76-94, Jun. 1988.

European Pharmacopoeia Commission, "Peritoneal Dialysis, Solutions for," in *European Pharmacopoeia*, $3^{rd}$ edition, Strasbourg, Germany, Council of Europe, 1997, pp. 1301-1303.

Extract from "Thrombose-Forum, *Antithrombotika, Sylvia Haas*," 2004, Chronomed Verlag, 4 pages.

Fischer, "Essentials of anticoagulation in hemodialysis," *Hemodialysis International* 11: 178-189, 2007.

Flanigan et al., "Regional Hemodialysis Anticoagulation: Hypertonic Tri-Sodium Citrate or Anticoagulant Citrate Dextrose-A," *American Journal of Kidney Diseases* 27(4): 519-524, Apr. 1996.

Glaser et al., "Haemodialysis Without Heparin is Possible," *The Lancet* 2: 579-580, Sep. 15, 1979.

Golberg, "Pharmacology of Parenteral Iron Preparations," in Wallerstein and Mettier (eds.), *Iron in Clinical Medicine*, University of California Press, Berkeley and Los Angeles, 1958, pp. 74-92.

Gordon et al., "Pyrogenic Reactions in Patients Receiving Conventional, High-Efficiency, or High-Flux Hemodialysis Treatments with Bicarbonate Dialysate Containing High Concentrations of Bacteria and Endotoxin," *J. Am. Soc. Nephrol.* 2: 1436-1444, 1992.

Guest et al., "Functional consequences of correction of metabolic acidosis in hemodialysis patients," *J. Am. Soc. Nephrol.* 8: 236A, Abstract No. A1090, Sep. 1997.

Gupta et al., "Dialysate iron therapy: Infusion of soluble ferric pyrophosphate via the dialysate during hemodialysis," *Kidney International* 55(5): 1891-1898, May 1999.

Jander and Blasius, *Lehrbuch der analytischen und präparativen anorganischen Chemie* (translated *Text book of analytical and preparative inorganic chemistry*), S. Hirzel, Verlag Stuttgart, Germany, 1973, Chapter 2.6.5.5.4, "Buffer Capacity," p. 66, translation.

Janssen et al., "Citrate Anticoagulation and Divalent Cations in Hemodialysis," *Blood Purif.* 12: 308-316, 1994.

Jennrich et al., "Unbalanced Repeated-Measures Models with Structured Covariance Matrices," *Biometrics* 42: 805-820, Dec. 1986.

Kossmann et al., 55% Heparin Reduction Using Citrate Dialysate (Citrasate®), http://www.dialmedsupply.com/citrasate/PDF/HeparinReduction.pdf, download date Nov. 24, 2009.

Křížek et al., "Influence of Hemodialysis on Selenium Blood Levels," *Sborník lékařský* 101(3): 241-248, 2000.

Lin et al., "Influence of Rapid Correction of Metabolic Acidosis on Serum Osteocalcin Level in Chronic Renal Failure," *ASAIO Journal* 40: M440-M444, 1994.

Napolitano et al., "Thyroid Function and Plasma Selenium in Chronic Uremic Patients of Hemodialysis Treatment," *Biological Trace Element Research* 55(1/2): 221-230, Oct./Nov. 1996.

Nilsson, "Citrate vs. Acetate in Bicarbonate-Based Dialysis Fluid—What Does it Mean Clinically?," Gambro Lundia AB [White Paper], pp. 1-5, 2012.

Perdrix et al., "Anticoagulation regionale par le citrate au cours de l'hémodialyse chez les patients à haut risque hémorragique," *Ann. Fr. Anesth Réanim.* 7:31-35, 1988.

Pinnick et al., "Regional Citrate Anticoagulation for Hemodialysis in the Patient at High Risk for Bleeding," *The New England Journal of Medicine* 308(5): 258-261, Feb. 3, 1983.

PR Newswire (May 28, 1986), "A hemodialysis grade of Arm & Hammer sodium bicarbonate is introduced by the chemicals division of Church & Dwight Co. Inc. for use in products used in hemodialysis," URL=http://www.highbeam.com/doc/1G1-4256216.html/print, download dated Feb. 22, 2012, 2 pages.

(56) References Cited

OTHER PUBLICATIONS

Reaich et al., "Correction of acidosis in humans with CRF decreases protein degradation and amino acid oxidation," *Am. J. Physio.*7: E230-E235, 1993.
Sanders et al., "Hemodialysis Without Anticoagulation," *American Journal of Kidney Diseases* 5(1): 32-35, Jan. 1985.
Schwab et al., "Hemodialysis without Anticoagulation—One-Year Prospective Trial in Hospitalized Patients at Risk for Bleeding," *The American Journal of Medicine* 83: 405-410, 1987.
Sonikian et al., "Potential Effect of Metabolic Acidosis on β2-Microglobulin Generation: In Vivo and In Vitro Studies," *J. Am.Soc. Nephrol.* 7(2): 350-356, 1996.
Šrámek et al., "Continuous venovenous hemodiafiltration (CVVHDF) with citrate anticoagulation in the treatment of a patient with acute renal failure, hypercalcemia, and thrombocytopenia," *Intensive Care Med* 24: 262-264, 1998.
Suh and Wadhwa, "Iron Dextran Treatment in Peritoneal Dialysis Patients on Erythropoietin," *Adv. Perit. Dial.* 8: 464-466, 1992.
Van Der Meulen et al., "Citrate anticoagulation and dialysate with reduced buffer content in chronic hemodialysis," *Clinical Nephrology*, 37(1): 36-41, 1992.
Wu et al., "Clinical application of erythropoietin (EPO) and chalybeate", Journal of Postgraduates of Medicine 24(4): 50-52, Apr. 2001, with English translation.
Yu et al., "Study of application of zinc-containing dialysate in hemodialysis patients", Chinese Journal of Nephrology 11(5): 281, Oct. 1995, with English translation.
Zawada, Jr., "Indications for Dialysis," in John T. Daugirdas, M.D. and Todd S. Ing, M.D. (eds.), *Handbook of Dialysis*, Little, Brown and Company, 1994, pp. 3-9.
Zima et al., "Trace Elements in End-Stage Renal Disease," *Blood Purification* 17(1): 187-198, 1999.
Zima et al., "Trace Elements in Hemodialysis and Continuous Ambulatory Peritoneal Dialysis Patients," *Blood Purcation* 16(1): 253-260, Jan.-Feb. 1998.
"NKF-DOQI Clinical Practice Guidelines for the Treatment of Anemia of Chronic Renal Failure," American Journal of Kidney Diseases 30(4 Suppl. 3): S192-S240, Oct. 1997.
Abstract of DE 41 14 908, Nov. 12, 1992, esp@cenet database.
Response to Official Action from European Patent Office, dated Jun. 7, 2010, for Patent Application No. 06006408.6, 5 pages.
Response to Official Action from European Patent Office, dated Sep. 21, 2011, for Patent Application No. 06006408.6, 32 pages.
Response to Official Action from European Patent Office, dated Jul. 2, 2012, for Patent Application No. 06006408.6, 18 pages.
Response to Official Action from European Patent Office, dated Nov. 27, 2012, for Patent Application No. 06006408.6, 6 pages.
Response to Official Action from European Patent Office, dated Feb. 8, 2013, for Patent Application No. 06006408.6, 4 pages.
Response to Official Action from European Patent Office, dated May 9, 2013, for Patent Application No. 06006408.6, 3 pages.
Response to 71(3) Communication from European Patent Office, dated Jul. 30, 2013, for Patent Application No. 06006408.6, 4 pages.
European Search Report from European Patent Office, dated Dec. 2, 2008, for Patent Application No. 06006408.6, 6 pages.
Replacement European Search Report from European Patent Office, dated Dec. 18, 2008, for Patent Application No. 06006408.6, 7 pages.
Extended European Search Report from European Patent Office, dated May 25, 2009, for Patent Application No. 06006408.6, 12 pages.
Article 94(3) Communication from European Patent Office, dated Jun. 20, 2011, for Patent Application No. 06006408.6, 3 pages.
Invitation Pursuant to Article 94(3) and Rule 71(1) EPC from European Patent Office, dated Jan. 20, 2012, for Patent Application No. 06006408.6, 3 pages.
Communication pursuant to Rule 114(2) EPC from European Patent Office, dated Mar. 6, 2012, for Patent Application No. 06006408.6, 62 pages.
Article 94(3) Communication from European Patent Office, dated Mar. 20, 2012, for Patent Application No. 06006408.6, 22 pages.
Invitation Pursuant to Article 94(3) and Rule 71(1) EPC from European Patent Office, dated Dec. 5, 2012, for Patent Application No. 06006408.6, 3 pages.
Communication pursuant to Rule 114(2) EPC from European Patent Office, dated Jan. 10, 2013, for Patent Application No. 06006408.6, 20 pages.
Invitation Pursuant to Article 94(3) and Rule 71(1) EPC from European Patent Office, dated Feb. 14, 2013, for Patent Application No. 06006408.6, 3 pages.
Communication pursuant to Rule 114(2) EPC from European Patent Office, dated Mar. 20, 2013, for Patent Application No. 06006408.6, 7 pages.
Result of Consultation with Examiner of European Patent Office, dated Apr. 17, 2013, for Patent Application No. 06006408.6, 3 pages.
Communication under Rule 71(3) EPC from European Patent Office, dated Jul. 22, 2013, for Patent Application No. 06006408.6, 7 pages.
*Blutreinigungsverfahren—Technik und Klinik*, Hans Eduard Franz and Walter H. Hörl, Editors, Georg Thieme Verlag, 5th Edition, 1997, 10 pages, with English translation.
*Dialyse für Krankenpflegeberufe*, Hans E. Franz, Editor, Georg Thieme Verlag, 1996, 5 pages, with English translation.
*Dialyse-behandlung—Ein Ratgeber für Patienten und Pflegepersonal*, Prof. Dr. med. Hans-Eduard Franz, Georg Thiem Verlag, 3rd Edition, 1984, 5 pages, with English translation.
*Hämodialyse Technik und Anwendung—Ein Kompendium für Ärzte, Pflegepersonal und Techniker*, Günter Meyer, Pabst Science Publishers, 1994, 5 pages, with English translation.
"Haemodialysis, Solutions for," Extract from *European Pharmacopoeia*, 1997, p. 921.
*Hämodialyse-Kurs für Ärzte und Pflegepersonal mit Fragen und Antworten*, Aldo Colombi, Enke Verlag, 5th Edition, 1991, 5 pages, with English translation.
Notice of Opposition from Opponent Gambro Lundia AB, mailed Jun. 10, 2014, for European Patent No. 1721606, 6 pages.
Submission from Opponent Gambro Lundia AB, mailed Jun. 10, 2014, for European Patent No. 1721606, 27 pages.
Declaration of Emma Lindeberg dated Jun. 10, 2014 from Opposition to EP 1 721 606, 3 pages.
Declaration of Robin Callan dated Sep. 12, 2011 from Opposition to EP 1 721 606, 6 pages.
Notice of Opposition from Opponent Fresenius Medical Care AG & Co. KGaA, mailed Jun. 11, 2014, for European Patent No. 1721606, 5 pages.
Submission from Opponent Fresenius Medical Care AG & Co. KGaA (and English translation), mailed Jun. 11, 2014, for European Patent No. 1721606, 41 pages.
Notice of Opposition from Opponent D_MED Consulting AG, mailed Jun. 11, 2014, for European Patent No. 1721606, 5 pages.
Notice of Opposition from Opponent INTERMEDT Medizin & Technik GmbH, mailed Jun. 11, 2014, for European Patent No. 1721606, 5 pages.
Submission from Opponents D-MED Consulting AG and INTERMEDT Medizin & Technik GmbH, mailed Jun. 11, 2014, for European Patent No. 1721606, 19 pages.
Submission from Opponent Intermedt GmbH and D-MED Consulting AG, mailed Feb. 24, 2015, for European Patent No. 1721606, 2 pages, with translation.
Response from Patentee Advanced Renal Technologies, mailed Mar. 13, 2015, for European Patent No. 1721606, 2 pages.
Declaration of Robin Callan dated Dec. 23, 2014 for Response to Opposition to European Patent No. 1721606, 6 pages.
Response of the Patentee Advanced Renal Technologies to Oppositions filed by Fresenius Medical Care AG & Co. KGAA, Gambro Lundia AB, Intermedt Medizin & Technik GmbH and D Med Consulting AG, mailed Dec. 31, 2014, for European Patent No. 1721606, 34 pages.
Gambro SelectBag® Citrate product information for BiCart Select® Citrate System, 2012, 2 pages.
Submission from Opponent Fresnius Medical Care AG & Co. KGaA, mailed Jan. 16, 2015, for European Patent No. 1721606, 22 pages, with translation.

(56) References Cited

OTHER PUBLICATIONS

Response from Patentee Advanced Renal Technologies, mailed Jan. 30, 2015, for European Patent No. 1721606, 3 pages.
Submission from Opponent Fresnius Medical Care AG & Co. KGaA, mailed Feb. 13, 2015, for for European Patent No. 1721606, 4 pages, with translation.
Summons to attend oral proceedings, mailed Jun. 15, 2015, for European Patent No. 1721606, 22 pages.
Fresenius Medical Care 1998 Annual Report, 92 pages.
Sands et al., "Effects of Citrate Acid Concentrate (Citrasate®) on Heparin N Requirements and Hemodialysis Adequacy: A Multicenter, Prospective Noninferiority Trial," *Blood Purif.* 33: 199-204, 2012.
Submission from Opponent Fresenius Medical Care AG & Co. KGaA, mailed Sep. 25, 2015, for European Patent No. 1721606, 7 pages.
Faber et al., "Citrate haemodialysis," *Netherlands Journal of Medicine* 37: 219-224 1990.
BiCart Select® Citrate System Brochure, 2012, 8 pages.
Submissions in Response to Summons to Attend Oral Proceedings; Auxiliary Requests; and Declarations of Dr. Mitra (2) from Patentee Advanced Renal Technologies, filed Sep. 25, 2015, for opposition proceedings of European Patent No. 1721606, 68 pages.

\* cited by examiner

BUFFERED COMPOSITIONS FOR DIALYSIS

CROSS-REFERENCE TO RELATED APPLICATIONS

This application is a continuation of U.S. patent application Ser. No. 13/789,391, filed Mar. 7, 2013 (now pending); which is a divisional of U.S. patent application Ser. No. 12/684,546, filed Jan. 8, 2010 (now pending); which is a divisional of U.S. patent application Ser. No. 10/606,150, filed Jun. 24, 2003 (now U.S. Pat. No. 7,670,491 issued Mar. 2, 2010); which is a continuation-in-part of U.S. patent application Ser. No. 09/421,622, filed Oct. 19, 1999 (now U.S. Pat. No. 6,610,206, issued Aug. 26, 2003); which application claims the benefit of U.S. Provisional Patent Application No. 60/105,049, filed Oct. 20, 1998. These applications are incorporated herein by reference in their entireties.

BACKGROUND OF THE INVENTION

1. Field of the Invention

The present invention relates to therapeutic compositions, and particularly to dialysate compositions.

2. Description of the Related Art

When functioning correctly, the kidneys help the body maintain a normal internal environment called homeostasis. Kidneys help accomplish this normal balance by ridding the body of excess fluids and metabolic waste products (toxins) as well as maintaining precise levels of glucose and electrolytes. Kidney failure can be caused by multiple factors. However, regardless of why a person's kidneys fail, the failure results in the accumulation of excess fluid and toxic waste in that person's body. This uremic poisoning eventually causes death unless the waste material is removed by some artificial means. Hemodialysis is the most common therapeutic measure for a person whose kidneys no longer perform their blood purifying function. Another common type of dialysis is peritoneal dialysis (PD).

Dialysate is the fluid utilized in dialysis, where dialysate serves to 'clean' the blood of kidney failure patients. During hemodialysis, the patient's blood is circulated on one side of a membrane within a dialyzer (i.e., artificial kidney), while dialysate flows on the other side of the membrane. Since blood and dialysate are separated by a semipermeable membrane, movement of molecules can occur between the blood and dialysate. Although the membrane pores are too small to permit blood cells and proteins to leave the blood, the pores allow waste products to be transferred from the blood to the dialysate.

Peritoneal dialysis utilizes the patient's peritoneal membrane as a dialysis membrane. Upon instilling a volume of peritoneal dialysate into the peritoneal cavity, osmotic pressure and a diffusion gradient cause excess fluid and waste products to leave the blood by crossing the peritoneal membrane and accumulate in the peritoneal cavity containing the dialysis fluid. After a sufficient dwell time, the spent peritoneal dialysate together with the accumulated excess fluid and waste products are drained from the peritoneal cavity.

Today, virtually all dialysate for hemodialysis is made at the site of treatment (in a hemodialysis machine) by mixing (1) treated water, (2) an acid concentrate, and (3) a base concentrate. Because the base concentrate typically contains sodium bicarbonate as the primary basic material, dialysate made by mixing these ingredients is commonly known as bicarbonate dialysate. Bicarbonate dialysate is almost universally made in the hemodialysis machine, through the use of a "three-stream" proportionate pumping mechanism wherein the treated water, liquid 'acid concentrate' and liquid bicarbonate (base) concentrate are combined. One patient typically requires 120 liters or more of dialysate for a single hemodialysis treatment. Chronic kidney failure patients are treated 3 times per week, 52 weeks per year.

The concentrates are supplied to the dialysis clinic in two forms; the 'acid concentrate' is generally supplied as a liquid and the bicarbonate is shipped as a dry powder. The acid concentrate typically contains sodium chloride, calcium chloride, potassium chloride, magnesium chloride, dextrose and sufficient acid (acetic acid) for pH balance. The precise composition of the acid concentrate to be used in a specific dialysis session is determined by a doctor's prescription.

Prior to a patient's treatment session, a jug of liquid acid concentrate is obtained. Generally, this jug of concentrate is drawn from a larger tank or drum of the acid concentrate. A staff member of the dialysis clinic also prepares a jug of sodium bicarbonate concentrate by mixing a quantity of powdered sodium bicarbonate with a specific quantity of treated water. Separate concentrated solutions of 'acid' and bicarbonate are necessary because combining concentrated acid and base solutions would cause the precipitation of calcium and magnesium carbonates. After proper mixing, the final dialysate has the concentrations prescribed by the physician.

As noted, kidney failure patients accumulate excess fluids and normally excreted substances in their blood, most notably, blood urea nitrogen (BUN) and creatinine. In fact, the reduction in the blood levels of these two substances is generally used to gauge the efficiency and overall effectiveness of dialysis. Often the efficiency of dialysis can be compromised by a number of factors, one of which could be the blockage of dialyzer membrane pores by clotted blood.

Additionally, many kidney failure patients suffer from chronic acidosis because their kidneys are not able to remove acid. Traditionally, one of the several goals of hemodialysis treatment is the correction of acidosis by providing higher than normal amounts of bicarbonate in the dialysate to buffer the excess acid in the blood. However, despite infusing "extra" bicarbonate during hemodialysis, normal blood bicarbonate levels are not sustained in many patients between hemodialysis treatments.

Accordingly, there is a need in the art for improved dialysate formulations that increase the efficiency of the hemodialysis treatment. The present invention is directed to meeting this need and provides additional related advantages as disclosed herein.

BRIEF SUMMARY OF THE INVENTION

The present invention provides compositions, termed dialysate precursor compositions, which may be diluted with water and mixed with a base to thereby form a dialysate composition. The dialysate precursor composition, as well as the dialysate compositions prepared therefrom, contain citric acid and an effective amount of a buffering agent selected from acetate and/or lactate. The buffering agent requires a physiologically acceptable amount of citrate to maintain the desired pH of the dialysate.

In one embodiment, the invention provides a dialysate precursor composition. This composition contains, at a minimum, water; chloride at a concentration ranging from about 1,000 to about 7,000 mEq/L; citrate at a concentration ranging from about 20 to about 900 mEq/L; at least one buffering anion selected from acetate and/or lactate at a concentration ranging from about 0.01 to about 150 mEq/L; and at least one physiologically-acceptable cation. In a related embodiment, the invention provides a dry dialysate precursor composition which, upon mixing with water, provides an aqueous composition having the above-recited components in the above-recited concentrations. In one embodiment the dry dialysate precursor composition is a pellet or tablet, while in another embodiment the dry dialysate precursor composition is a powder.

In another embodiment, the invention provides a dialysate composition. This dialysate composition contains, at a minimum, treated water; chloride at a concentration ranging from about 20 to about 200 mEq/L; citrate at a concentration ranging from about 0.5 to about 30 mEq/L; at least one buffering anion selected from acetate and/or lactate at a concentration ranging from about 0.01 to about 4.5 mEq/L; base including bicarbonate; and at least one physiologically-acceptable cation. In a related embodiment, the invention provides a dry dialysate composition which, upon mixing with water, provides an aqueous composition having the above-recited components in the above-recited concentrations. In one embodiment the dry dialysate composition is a pellet or tablet, while in another embodiment the dry dialysate composition is a powder.

In another embodiment, the present invention provides a method of forming a dialysate precursor composition. The method includes the step of mixing together treated water, chloride, citrate, at least one buffering anion selected from acetate and/or lactate, and at least one physiologically-acceptable cation to provide a composition having chloride at a concentration ranging from about 1,000 to about 7,000 mEq/L, citrate at a concentration ranging from about 20 to about 900 mEq/L, and at least one buffering anion selected from acetate and lactate at a concentration ranging from about 0.01 to about 150 mEq/L. In a related embodiment, the invention provides a method of forming a dialysate precursor composition which includes the step of mixing water with a dry dialysate precursor composition comprising the above-recited components, so as to provide an aqueous composition having the above-recited component concentrations. In one embodiment, the dry dialysate precursor composition is a pellet or tablet, while in another embodiment the dry dialysate precursor composition is a powder.

In another embodiment, the present invention provides a method of forming a dialysate composition. The method includes the step of mixing the dialysate precursor composition with an aqueous bicarbonate-containing solution. The dialysate precursor composition contains, at a minimum, treated water, chloride, citrate, at least one buffering anion selected from acetate and lactate, and at least one physiologically-acceptable cation to provide a concentrate having chloride at a concentration ranging from about 44 to about 143 mEq/L, citrate at a concentration ranging from about 1.5 to about 30 mEq/L, and at least one buffering anion selected from acetate and lactate at a concentration ranging from about 0.01 to about 3.6 mEq/L.

In other embodiments, the present invention provides compositions prepared according to the afore-described methods.

In another embodiment, the present invention provides an aqueous acid-concentrate composition which contains water, chloride at a concentration of about 1,000 to about 7,000 mEq/L; citrate at a concentration ranging from about 20 to about 900 mEq/L; and sufficient physiologically-acceptable cations to provide for a neutral composition. This acid-concentrate composition has a pH of less than 4, and does not contain any of acetate, bicarbonate or lactate.

In a related embodiment, the invention provides a dry acid-concentrate precursor composition comprising the above-recited components (absent the water) which, upon mixing with water, provides the aqueous acid-concentrate composition having the indicated components in the indicated concentrations. In one embodiment, the dry acid-concentrate precursor composition is a pellet or tablet, while in another embodiment the dry acid-concentrate precursor composition is a powder.

The magnesium concentration is preferably less than or equal to 2 mEq/L, and the calcium concentration is preferably less than or equal to 4.5 mEq/L, and the bicarbonate concentration is preferably within the range of 25-40 mEq/L. The calcium and magnesium concentrations should be adjusted to higher values as the amount of citrate in the composition increases, in order to compensate for citrate's binding to serum calcium and/or magnesium.

In another embodiment, the present invention provides sterile compositions specifically suited for peritoneal dialysis. According to one embodiment, the invention provides a peritoneal dialysate composition comprising treated water, citrate at a concentration of about 0.5-30 mEq/L; chloride at a concentration of about 20-200 mEq/L; bicarbonate at a concentration of about 5-100 mEq/L assuming all carbonate-containing species are in the bicarbonate form, glucose at a concentration of about 10-100 g/L; and a sufficient number of physiologically-acceptable cations to neutralize all of the citrate, chloride, bicarbonate, and any other anionic species that may be present in the composition. In another embodiment, the invention provides a composition for peritoneal dialysis as described above, but without any water. This embodiment thus provides a dry composition, to which sterile water may be added in order to form a peritoneal dialysate.

DETAILED DESCRIPTION OF THE INVENTION

In one aspect, the present invention provides compositions, termed dialysate precursor compositions, which contain, or are prepared from, components including water, chloride, citrate, at least one buffering anion preferably selected from acetate and/or lactate, and at least one physiologically-acceptable cation. The dialysate precursor composition, upon mixing with a base and with dilution, forms a biocompatible composition that can be used for either hemodialysis or peritoneal dialysis. In a related aspect, the invention provides a dry dialysate precursor composition which, upon mixing with water, provides an aqueous composition having the above-recited components. In one embodiment the dry dialysate precursor composition is a pellet or tablet, while in another embodiment the dry dialysate precursor composition is a powder.

As discussed in more detail below, the presence of some buffering anion, e.g., an anion selected from acetate and/or lactate, in the dialysate precursor composition allows the dialysate precursor composition to be used as the acid concentrate in a standard three-stream dialysis machine, along with standard base (i.e., bicarbonate) concentrate, thereby mitigating problems associated with fluctuations in the pH of the dialysate during a dialysis treatment. Absent the buffering anion, the dialysate can have pH and/or conductivity properties which are outside the ranges considered acceptable by health care professionals. Prior to a more extended discussion of the compositions of the invention, and the properties thereof, the primary ingredients of the compositions will be described.

As used herein, "chloride" refers to anionic chloride. Thus, the term "chloride" includes anionic chloride and the salt forms thereof, such as may be formed from chloride anion(s) and physiologically-acceptable cation(s). The term "chloride" is not intended to include compounds wherein the chloride atom is covalently bonded to, for example, a carbon atom in an organic molecule. Exemplary physiologically-acceptable cations include, without limitation, hydrogen ions (i.e., protons), metal cations, and ammonium cations. Metal cations are generally preferred, where suitable metal cations include, but are not limited to, the cationic forms of sodium, potassium, magnesium and calcium. Of these, sodium and potassium are preferred, and sodium is more preferred. When iron or trace element is desirably included in the composition, the metal cation may be iron cation (i.e., ferric or ferrous cation) or may be a cation of a trace element, e.g., selenium or zinc cation. A composition containing chloride salts may contain a mixture of physiologically-acceptable cations.

In one embodiment, the chloride in the precursor dialysate composition is present at a concentration ranging from about 1,000 to about 7,000 mEq/L, preferably from about 2,000 to about 5,000 mEq/L. In general, the concentrations of the components of present precursor dialysate composition are individually prescribed by a physician to reduce, increase, or normalize the concentrations of various components of the patient's blood, plasma, or serum. Accordingly, the precise concentration of chloride in the precursor dialysate composition, and the dialysate composition prepared therefrom, will be determined by a physician according to principles known in the art.

As used herein, "citrate" refers to a citrate anion, in any form, including citric acid (citrate anion complexed with three protons), salts containing citrate anion, and partial esters of citrate anion. Citrate anion is an organic, tricarboxylate with the following chemical formula:

Citric acid, which has been assigned Chemical Abstracts Registry No. 77-92-2, has the molecular formula $HOC(CO_2H)(CH_2CO_2H)_2$ and a formula weight of 192.12 g/mol. A citrate salt (i.e., a salt containing citrate anion) is composed of one or more citrate anions in association with one or more physiologically-acceptable cations. Exemplary physiologically-acceptable cations include, but are not limited to, protons, ammonium cations and metal cations. Suitable metal cations include, but are not limited to, sodium, potassium, calcium, and magnesium, where sodium and potassium are preferred, and sodium is more preferred. A composition containing citrate anion may contain a mixture of physiologically-acceptable cations.

A partial ester of a citrate anion will have one or two, but not all three, of the carboxylate (i.e., —COO$^-$) groups of citrate anion in an ester form (i.e., —COO—R, where R is an organic group). In addition to one or two R groups, the partial ester of a citrate anion will include one or two physiologically-acceptable cations (so that the total of the R group(s) and cation(s) equals three). The R group is an organic group, preferably a lower alkyl.

The citrate is preferably in association with protons and/or metal cations. Exemplary of such citrate compounds are, without limitation, citric acid, sodium dihydrogen citrate, disodium hydrogen citrate, trisodium citrate, trisodium citrate dihydrate, potassium dihydrogen citrate, dipotassium hydrogen citrate, calcium citrate, and magnesium citrate. In one embodiment, the citrate is present in the dialysate precursor composition in the form of one or more of citric acid, sodium dihydrogen citrate, disodium hydrogen citrate, potassium dihydrogen citrate, or dipotassium hydrogen citrate.

In a preferred embodiment, citric acid provides the source for the citrate anions. In this embodiment, the citric acid functions as the main acidifying agent of the precursor composition. Citric acid is a relatively inexpensive physiological acid that, under ambient conditions, is in the form of a dry chemical powder, crystal, pellet or tablet. Any physiologically tolerable form of citric acid may be used to introduce citrate anions to the composition. For instance, the citric acid may be in the form of a hydrate, including a monohydrate.

Citrate has been previously recognized to be able to function as an anti-coagulant in the bloodstream by binding calcium. Accordingly, the citrate concentration of the dialysate precursor composition should be selected in view of its anti-coagulation properties. Unless other measures are taken, the citrate concentration should not exceed about 900 mEq/L, and is preferably not more than about 200 mEq/L. When citrate concentrations of 200-900 mEq/L are employed, the magnesium and/or calcium concentration of the dialysate precursor composition must be increased.

Although the citrate concentration should not be so great that it detrimentally affects the coagulation properties of blood, the concentration of citrate should be sufficiently high that it will be effective to achieve and maintain the pH of the final dialysate composition at a physiologically-acceptable pH. Typically, a citrate concentration that is one-quarter or less of the amount needed to achieve anti-coagulation can provide a dialysate composition with a physiologically-acceptable pH. Thus, the present dialysate precursor composition should have a minimum citrate concentration of about 20 mEq/L in order to provide the desired dialysate pH. In one embodiment, the dialysate precursor composition contains citrate at a concentration ranging from about 20 to about 900 mEq/L and in a preferred embodiment the composition contains citrate at a concentration ranging from about 70 to about 150 mEq/L. In a related embodiment, the invention provides a dry dialysate precursor composition which, upon mixing with water, produced a dialysate precursor composition that contains citrate at a concentration ranging from about 20 to about 900 mEq/L and in a preferred embodiment the composition contains citrate at a concentration ranging from about 70 to about 150 mEq/L.

Although citrate functions as an acidifying agent to lower the pH of a dialysate composition, in one aspect the present invention introduces a buffering anion to the dialysate precursor composition in order to maintain the pH of the final dialysate composition within a physiologically-acceptable range. As used herein, "buffering anion" refers to a physiologically acceptable anion that adjusts and regulates the pH of a composition. Suitable buffering anions include, for example, acetate, lactate, and mixtures thereof (i.e., acetate and/or lactate), which are compounds that will minimize changes in hydrogen ion concentration of a dialysate composition. As used herein, the phrase "lactate and/or acetate" means that either lactate alone, acetate alone, or a mixture of lactate and acetate may be used, or present, in the composition.

As used herein, "acetate" refers to an acetate anion, in any form, including acetic acid and salts of acetic acid. Acetate is an organic, monocarboxylate with the formula $H_3C—COO^-$. The acetate salt is composed of one or more acetate anions in association with one or more physiologically-acceptable cations. Exemplary physiologically-acceptable cations include, but are not limited to, protons, ammonium cations and metal cations, where metal cations are preferred. Suitable metal cations include, but are not limited to, sodium, potassium, magnesium and calcium, where sodium and potassium are preferred, and sodium is more preferred.

Exemplary acetate compounds of the present invention include, but are not limited to, acetic acid, sodium acetate, sodium acetate trihydrate, potassium acetate, calcium acetate, calcium acetate monohydrate, magnesium acetate, and magnesium acetate tetrahydrate. In one embodiment, the acetate of the dialysate precursor composition is present in the form of sodium acetate or potassium acetate, and in a preferred embodiment, acetate is in the form of sodium acetate.

As used herein, "lactate" refers to a lactate anion, in any form, including lactic acid and salts of lactic acid. Lactate is an organic, monocarboxylate with the formula $H_3C-CH(OH)-COO^-$. A lactate salt is composed of one or more lactate anions in association with one or more physiologically-acceptable cations. Exemplary physiologically-acceptable cations include, but are not limited to, protons, ammonium cations and metal cations, where metal cations are preferred. Suitable metal cations include, but are not limited to, sodium, potassium, magnesium and calcium, where sodium and potassium are preferred, and sodium is more preferred. When iron or trace element is desirably included in the composition, the metal cation may be iron cation (i.e., ferric or ferrous cation) or may be a cation of a trace element, e.g., selenium or zinc cation.

Exemplary lactate compounds of the present invention include, but are not limited to, lactic acid, sodium lactate, potassium lactate, calcium lactate and magnesium lactate trihydrate. In one embodiment, the lactate of the dialysate precursor composition is present in the form of sodium lactate or potassium lactate, and most preferably lactate is in the form of sodium lactate. When iron or trace element is desirably included in the composition, the lactate may be complexed with iron (i.e., ferric or ferrous lactate) or may be complexed with a trace element, e.g., selenium or zinc cation.

In general, the dialysate precursor composition will typically contain more equivalents of citrate than equivalents of buffering anion. The precursor composition preferably contains more equivalents of citrate than equivalents of acetate, lactate, or lactate+acetate. In one embodiment, the dialysate precursor composition contains citrate at a concentration ranging from about 20 to about 900 mEq/L together with a buffering anion selected from acetate and/or lactate at a concentration ranging from about 0.01 to about 150 mEq/L. In a preferred embodiment the composition contains citrate from about 70 to about 150 mEq/L and a buffering anion selected from acetate and/or lactate at a concentration ranging from about 0.3 to about 125 mEq/L. In a related embodiment, the present invention provides dry compositions (e.g., pellets, tablets, powder) which upon mixing with water provide the dialysate precursor compositions described above.

As the amount of citrate in the dialysate precursor composition is increased, it tends to lower the pH of the dialysate made with the precursor. With a lower dialysate pH, there is not as much need to buffer the precursor to ensure that the dialysate pH does not rise to a physiologically unacceptable level. Therefore, as a general rule, as higher equivalents of citrate are used in the dialysate precursor composition, less equivalents of buffering anion are required. Conversely, as less equivalents of citrate are used in the dialysate precursor composition, more equivalents of a buffering anion are required.

As used herein, the phrase "physiologically-acceptable cations" refers to cations normally found in the blood, plasma, or serum of a mammal, or cations that may be tolerated when introduced into a mammal. Suitable cations include protons, ammonium cations and metal cations. Suitable metal cations include, but are not limited to, the cationic forms of sodium, potassium, calcium, and magnesium, where sodium and potassium are preferred, and sodium is more preferred. An ammonium cation, i.e., a compound of the formula $R_4N^+$ where R is hydrogen or an organic group, may be used so long as it is physiologically acceptable. In a preferred embodiment, the cation is selected from hydrogen (i.e., proton), sodium, potassium, calcium, magnesium, and combinations thereof.

When the pH of a dialysate composition begins to increase (i.e., the dialysate becomes more basic) during the course of a dialysis treatment, the buffering anion, when present in an effective amount, prevents the pH of the dialysate composition from rising beyond a physiologically-acceptable range. For compositions having the citrate concentrations described above, and to provide the desired buffering effect, the precursor composition should contain from about 0.01 to about 150 mEq/L of buffering anion, preferably selected from acetate, lactate and mixtures thereof. In a preferred embodiment, the precursor composition contains from about 0.3 to about 125 mEq/L of acetate and/or lactate. In one embodiment, the buffering anion is a mixture of acetate and lactate. In another embodiment, the buffering anion is acetate, and lactate is not present in the composition. In another embodiment, the buffering anion is lactate, and acetate is not present in the composition.

With peritoneal dialysate, in order to facilitate the diffusion between blood and dialysate, it is desirable to maintain an osmotic gradient between the fluids by adding an osmotic agent to the dialysate. The presence of an osmotic agent in the peritoneal dialysate will encourage excess fluid and metabolic waste byproducts to flow from the blood and into the dialysate. A suitable osmotic agent for the precursor dialysate composition is sugar. The sugar is preferably selected from glucose (e.g., dextrose), poly(glucose) (i.e., a polymer made from repeating glucose residues, e.g., icodextrin, made from repeating dextrose units), or fructose. While it is possible to make a dialysate precursor with no sugar, if sugar is to be added to the dialysate composition, it is generally dextrose. It is further appreciated that any biocompatible, non-sugar osmotic agent that functions as an equivalent could be a viable substitute. The sugar is typically present in the dialysate precursor composition at a concentration of less than about 2,700 g/L.

A patient's blood serum contains several components including, for example, proteins, carbohydrates, nucleic acids, and various ions. Typically, a dialysate composition prescribed by a physician is chosen to reduce, increase, or normalize the concentration of a particular component in the serum. Several cations may be prescriptively included as part of the precursor dialysate composition. Suitable cations may include, for example, sodium, potassium, calcium and magnesium. In the dialysate precursor composition, the preferred concentration range for sodium is from about 2,000 to about 5,000 mEq/L. The preferred concentration range for potassium is less than about 250 mEq/L. The preferred concentration range for calcium is less than about 250 mEq/L. The preferred concentration range for magnesium is less than about 100 mEq/L. As used herein, a concentration of less that about a recited value includes zero. In a related embodiment, the present invention provides dry compositions (e.g., tablets, pellets, powder, etc.) which upon mixing with water provide a dialysate precursor composition having the sodium, potassium, calcium, and magnesium concentrations recited above.

As used herein, "mEq/L" refers to the concentration of a particular dialysate component (solute) present in proportion to the amount of water present. More specifically, mEq/L refers to the number of milli-equivalents of solute per liter of water. Milli-equivalents per liter are calculated by multiplying the moles per liter of solute by the number of charged species (groups) per molecule of solute, which is then multiplied by a factor of 1,000. As an example, when 10 grams of citric acid are added to a liter of water, the citric acid is present at a concentration of 10 g/L. Anhydrous citric acid has a molecular weight of 192.12 g/mol; therefore, the number of moles per liter of citric acid, and consequently citrate anion (since there is one mole of citrate anion per mole of citric acid), is 10 g/L divided by 192.12 g/mol, which is 0.05 mol/L. Citrate anion has three negatively charged species in the form of carboxylate groups. Accordingly, the citrate concentration of 0.05 mol/L is multiplied by three and then by 1,000, in order to provide a concentration of citrate in terms of mEq/L, which in the present example is 156 mEq/L of citrate anion.

A preferred water of the invention is treated in order that it is essentially pyrogen-free and sterile, and at least meets the purity requirements established by the Association for the Advancement of Medical Instrumentation (AAMI) for dialysate compositions. The water may also be referred to as treated water or AAMI-quality water. A monograph describing water treatment for dialysate, monitoring of water treatment systems, and regulation of water treatment systems is available from AAMI (Standards Collection, Volume 3, Dialysis, Section 3.2 Water Quality for Dialysis, 3 ed., 1998, AAMI, 3330 Washington Boulevard, Arlington, Va. 22201). In addition, all of the other components of the precursor dialysate composition of the present invention are preferably at least United States Pharmacopeia (USP)-grade purity, which is generally a purity of about 95%. The purity of the components is preferably at least about 95%, more preferably at least about 98%, and more preferably at least about 99%.

The dialysate precursor composition of the present invention will typically have a pH ranging from about 1 to about 6.5, more typically from about 1 to about 4, more typically from about 2 to about 4, at a temperature of about 15° C. to about 40° C., before dilution with treated water and base to afford the dialysate composition.

In a preferred embodiment, the dialysate precursor composition contains components including chloride at a concentration ranging from about 2,000 to about 5,000 mEq/L; citrate at a concentration ranging from about 70 to about 150 mEq/L; acetate and/or lactate at a total concentration ranging from about 0.3 to about 125 mEq/L; at least one physiologically-acceptable cation selected from hydrogen, sodium at a concentration ranging from about 2,000 to about 5,000 mEq/L, potassium at a concentration of less than about 250 mEq/L, calcium at a concentration of less than about 250 mEq/L, and magnesium at a concentration of less than about 100 mEq/L; and glucose (preferably dextrose) at a concentration of less than about 2,700 g/L, where the composition meets or exceeds the AAMI standard set for dialysate. In one embodiment, the above-listed ingredients are the only active ingredients in the composition. In a related embodiment, the present invention provides a dry composition which, upon mixing with water, provides the dialysate precursor composition having the components and component concentrations indicated above.

The present invention provides a method of forming the precursor dialysate composition as described above. In this method, ingredients are mixed together so as to provide the dialysate precursor composition. Thus, a source of chloride, a source of citrate, and a source(s) of buffering anion (e.g., acetate and/or lactate) are mixed together with treated water, in amounts which ultimately provide the desired concentration of each, as set forth above. The non-aqueous components of the precursor dialysate composition may be pre-mixed and in the form of a powder, pellet, tablet or other dry form, which is then readily mixed with water so as to form the precursor dialysate composition. Suitable sources for these ingredients are well known in the art. Indeed, the chemical characteristics for the compounds used in the present invention, such as molecular weight and solubility, are available in the art such that one of ordinary skill in the art will know how to prepare the composition of the present invention. See, e.g., the Sigma and Aldrich catalogs from Sigma-Aldrich (Milwaukee, Wis.).

For example, the chloride source may be any of hydrochloric acid, sodium chloride, potassium chloride, magnesium chloride, ammonium chloride, or the like. The citrate source may be any of citric acid, sodium dihydrogen citrate, disodium hydrogen citrate, trisodium citrate, trisodium citrate dihydrate, potassium dihydrogen citrate, dipotassium hydrogen citrate, calcium citrate, magnesium citrate, or the like. The acetate source may be any of acetic acid, sodium acetate, sodium acetate trihydrate, potassium acetate, calcium acetate, calcium acetate monohydrate, magnesium acetate, magnesium acetate tetrahydrate, and the like. The lactate source may be any of lactic acid, sodium lactate, potassium lactate, calcium lactate, magnesium lactate trihydrate, and the like. Any or all of these chemicals are commercially available, in USP-grade if desired, from many chemical supply houses including, for example, Aldrich Chemical Co., Milwaukee Wis. The treated water may be obtained by following standard purification techniques, including, for example, distillation and reverse osmosis. Alternatively, the treated water may be purchased commercially. Such treated water is used in all, or nearly all, dialysis clinics and accordingly is well known to one of ordinary skill in the art.

In one embodiment, the invention provides a method of forming a dialysate precursor composition which includes the step of mixing water, chloride, citrate, at least one buffering anion selected from acetate and/or lactate, and at least one physiologically-acceptable cation, to provide a composition having chloride at a concentration ranging from about 1,000 to 7,000 mEq/L, citrate at a concentration ranging from about 20 to 900 mEq/L, and at least one buffering anion selected from acetate and/or lactate at a total concentration ranging from about 0.01 to 150 mEq/L. The non-aqueous components of the dialysate precursor composition may be pre-mixed and in the form of a dry powder, pellet, tablet, etc., so that the method entails mixing water with this dry pre-mixed composition.

In a preferred embodiment, sources of water, chloride, citrate, acetate and physiologically-acceptable cations are mixed so as to provide a composition having water, chloride at a concentration ranging from about 2,000 to about 5,000 mEq/L; citrate at a concentration ranging from about 70 to about 150 mEq/L; acetate at a concentration ranging from about 0.3 to about 125 mEq/L; at least one physiologically-acceptable cation selected from hydrogen, sodium at a concentration ranging from about 2,000 to about 5,000 mEq/L, potassium at a concentration of less than about 250 mEq/L, calcium at a concentration of less than about 250 mEq/L, magnesium at a concentration of less than about 100 mEq/L;

and glucose at a concentration of less than about 2,700 g/L, where the composition meets or exceeds the AAMI-quality standard set for dialysate.

In another aspect, the present invention provides a dialysate composition. The dialysate composition may, for example, be prepared from the dialysate precursor composition described above by adding treated water and a base, preferably bicarbonate, to the precursor composition. Upon the addition of base and water, the dialysate precursor composition provides a composition suitable for performing dialysis. As an alternative, a dry composition as also described previously may be combined with water and base in order to prepare the dialysate composition.

For example, bicarbonate concentrate, or diluted bicarbonate concentrate, may be added to the dialysate precursor composition, or diluted dialysate precursor composition, to provide a dialysate composition according to the present invention. Typically, one volume part of dialysate precursor composition is diluted with between 33 and 45 parts of diluted base concentrate, to provide the dialysate composition. The dialysate precursor will contain citrate (as the primary acidic ingredient of the acid concentrate), bicarbonate (as the primary basic ingredient of the base concentrate) and buffering anion preferably selected from acetate and/or lactate.

In one embodiment, the dialysate composition contains ingredients including treated water; chloride at a concentration ranging from about 20 to about 200 mEq/L; citrate at a concentration ranging from about 0.5 to about 30 mEq/L; at least one buffering anion selected from acetate and/or lactate at a concentration ranging from about 0.01 to about 4.5 mEq/L; bicarbonate; and at least one physiologically-acceptable cation.

In one embodiment, the dialysate composition includes one or more sugars selected from glucose (preferably dextrose), poly(glucose) (preferably, poly(dextrose), e.g., icodextrin), and fructose at a concentration of less than about 45 g/L. Instead, or in addition to sugar, the dialysate composition may contain one or more amino acids. Preferably, the dialysate composition contains water that meets or exceeds the purity requirements established by AAMI for dialysate and all other components have at least USP-grade purity. In another preferred embodiment, the dialysate composition has a pH of about 5 to about 8.5 at a temperature of about 25° C. to about 40° C., and more typically has a pH of about 6.4 and 7.6 at this temperature range, and preferably has a pH of about 7.2 to about 7.4.

In other embodiments, the dialysate composition contains ingredients including water, chloride at a concentration ranging from about 40 to about 150 (more preferably, from about 60 to about 120) mEq/L; citrate at a concentration ranging from about 1.5 to about 4.5 (more preferably, from about 2 to about 3) mEq/L; acetate and/or lactate at a total concentration ranging from about 0.01 to about 4.0 (more preferably, from about 0.2 to 0.5) mEq/L; bicarbonate at a concentration ranging from about 25 to about 45 mEq/L; at least one physiologically-acceptable cation selected from hydrogen, sodium at a concentration ranging from about 60 to about 190 (more preferably, from about 70 to about 150) mEq/L, potassium at a concentration of less than about 5 mEq/L, calcium at a concentration of less than about 5 mEq/L, and magnesium at a concentration of less than about 2 mEq/L; and glucose (preferably, dextrose) at a concentration of less than about 45 (preferably, less than about 8) g/L, where the combined composition meets or exceeds the AAMI-quality standard set for dialysate.

In the dialysate compositions of the present invention, including the precursors thereto, for either hemodialysis or peritoneal dialysis, in one embodiment of the invention the composition includes iron. Patients undergoing dialysis are oftentimes iron deficient, where iron deficiency is associated with anemia and other undesirable medical conditions. Currently, iron deficiency is most commonly addressed by either oral iron supplementation programs or by parenteral administration of iron. However, oral iron supplementation programs sometimes cause adverse gastrointestinal effects, and there is also the difficulty that patients do not rigorously follow the program. Parenteral administration of iron overcomes certain difficulties associated with oral iron administration and is the standard method if the patient is on peritoneal dialysis. For hemodialysis patients it is injected into the venous blood line of the dialysis apparatus during treatment, which adds inconvenience and cost. One aspect of the present invention addresses these problems by providing iron-containing dialysis compositions. As used in this context, the term "iron" refers to both the ferric and ferrous forms of iron, as well as complexes of iron.

The iron may be introduced into the composition in any convenient form that is also compatible with the well-being of the patient (see, e.g., "NKF-DOQI clinical practice guidelines for the treatment of anemia of chronic renal failure" *Am J. Kidney Dis.* 30:S192-S237, 1997). For example, iron dextran (ferric hydroxide dextran complex, CAS Registry No. 9004-66-4) is currently administered to hemodialysis patients via parenteral administration. (see, e.g., "Iron dextran treatment in peritoneal dialysis patients on erythropoietin" Perit. Dial. Bull. 8:464-466, 1992; and Goldberg, L., "Pharmacology of parenteral iron preparations" Iron in *Clinical Medicine* 78:74-92, 1958). In lieu of, or in addition to, dextran, the iron may be complexed with other sacchamides or polysaccharides, e.g., iron saccharate or gluconate complex. Any of these iron saccharide complexes may be included in a dialysate composition of the present invention. As another example, the iron may be introduced via ferric pyrophosphate (see, e.g., Gupta, A., et al. "Dialysate iron therapy: Infusion of soluble ferric pyrophosphate via the dialysate during hemodialysis" *Kidney International* 55:1891-1898, 1999). In order to create a water-soluble form of ferric pyrophosphate, the ferric pyrophosphate may be prepared by chemical reaction with citric acid and sodium hydroxide. As a final example, the iron may be introduced to the dialysate composition via either or both of ferric citrate (CAS Registry No. 3522-50-7) or ferrous citrate. In one aspect of the invention, the iron is introduced to the dialysate via an iron salt of citrate.

Regardless of the form in which the iron is added to the dialysate, the amount of iron being added should be a therapeutically effective amount. This amount will vary somewhat depending on the specific condition of the patient and the goals of the attending physician. However, generally, an iron concentration in dialysate ranging from 0.1 to 300 micrograms/deciliter will be a suitable concentration. Because this amount will typically vary from patient to patient, a commercial citrate-containing product may be prepared that does not contain any iron, and the product may be "spiked" with the desired amount of iron in the hospital or other site where the patient is undergoing the dialysis treatment.

In the dialysate compositions of the present invention, including the precursors thereto, for either hemodialysis or peritoneal dialysis, in one embodiment of the invention the composition includes one or more trace elements. Studies have shown that dialysis, and particularly maintenance dialysis, causes loss of trace elements from the patient undergoing the dialysis. The present invention provides compositions and methods to offset that loss of trace elements by incorporating trace elements into a composition of the present invention.

Any one or more trace elements may be included in a composition of the present invention (see, e.g., Zima, T., et al., *Blood Purif.* 17(4):187-198, 1999 and Zima, T. et al. "Trace *Blood Purif.* 16(5):253-260, 1998). For example, selenium may be included in a composition of the present invention (see, e.g., Krizek, M. et al. "Influence of hemodialysis on selenium blood levels" *Sb Lek* 101(3):241-248, 2000; and Napolitano G., "Thyroid function and plasma selenium in chronic uremic patients on hemodialysis treatment" *Biol. Trace Elem. Res.* 55(3):221-30, December 1996). Another trace element that may be included in a composition of the present invention is zinc. Chromium, manganese and molybdenum are yet three other trace elements that may be included in the dialysate composition.

The trace element may be added to the composition via any salt or complex of the element. For example, regardless of the identity of the trace element, in one aspect of the invention the element may be added to a composition of the present invention via its citrate salt. However, other suitable forms may be used, e.g., zinc sulfate for zinc, selenium sulfide for selenium. The amount of trace metal to be included in a composition of the present invention should be selected in view of the specific condition of the patient and the goal of the attending physician. However, generally, the Recommended Daily (or Dietary) Allowance (RDA) of trace elements, as set forth by the Food and Nutrition Board of the National Academy of Sciences/National Research Council, is a good guideline to follow (see, e.g., Recommended Dietary Allowances: National Academy of Sciences; 10th ed., 1989; see also Dietary Reference Intakes (DRIs): National Academy of Sciences, 1997). Because this amount may vary from patient to patient, a commercial citrate-containing product may be prepared that does not contain any trace elements, and the product may be "spiked" with the desired trace elements, in the desired amounts, in the hospital or other site where the patient is undergoing the dialysis treatment.

In another aspect, the present invention provides a method of forming a dialysate composition. In a preferred embodiment, the method includes combining the dialysate precursor composition, as described above, with a base concentrate, preferably a bicarbonate base concentrate, and treated water as needed to provide prescribed concentrations of solutes in the dialysate. The base concentrate contains water, bicarbonate, and has a pH of greater than 7. The pH will be greater than 7 because of the presence, in the concentrate, of one or more "bases." Base concentrate is currently used in most dialysis clinics. The base in a typical base concentrate is bicarbonate, also known as hydrogen carbonate, having the chemical formula $HCO_3$. Bicarbonate carries a net negative charge, and accordingly will be associated with a positively charged species. Suitable positively charged species include physiologically-acceptable metal cations such as the cationic forms of sodium, potassium, calcium and magnesium.

The base from which the base concentrate is almost universally prepared in dialysis clinics is sodium bicarbonate, and this is the preferred base in the present compositions and methods. The bicarbonate concentrate in a dialysate is preferably from about 25 to 40 mEq/L. Acetate base is not a preferred base.

Optionally, the sodium bicarbonate in a base concentrate may be replaced, in part, with a different physiologically-acceptable base. The anionic portion of a suitable replacement for sodium bicarbonate may be, for example, carbonate, lactate, citrate and acetate. Accordingly, the base for a base concentrate may be selected from the salt forms of any of bicarbonate and, optionally, carbonate, lactate, citrate and acetate. Also present in the salt forms will be one or more physiologically-acceptable cations selected from sodium, potassium, calcium and magnesium. These salts and acids are electronically neutral, i.e., there are an equal number of negative and positive charges.

Preferably, the dialysate precursor composition and the base concentrate are mixed so as to arrive at a dialysate composition that contains ingredients including water, chloride at a concentration ranging from about 40 to about 150 (more preferably, from about 60 to about 120) mEq/L; citrate at a concentration ranging from about 1.5 to 15.0, preferably from about 1.5 to about 4.5 (more preferably, from about 2 to about 3) mEq/L; acetate and/or lactate at a total concentration ranging from about 0.01 to about 4.0 (more preferably, from about 0.2 to 0.5) mEq/L; bicarbonate at a concentration ranging from about 25 to about 45 mEq/L; at least one physiologically-acceptable cation selected from hydrogen, sodium at a concentration ranging from about 60 to about 190 (more preferably, from about 70 to about 150) mEq/L, potassium at a concentration of less than about 5 mEq/L, calcium at a concentration of less than about 5 mEq/L, and magnesium at a concentration of less than about 2 mEq/L; and glucose (preferably, dextrose) at a concentration of less than about 45 (preferably, less than about 8) g/L, where the combined composition meets or exceeds the AAMI-quality standard set for dialysate. Higher concentrations of citrate could typically be used when a patient is simultaneously infused with excess calcium.

In dialysate compositions of the invention, the citrate-containing dialysate precursor composition is combined with the base concentrate so as to arrive at a final dialysate composition having a pH in the physiological range of 5 to 8.5, and preferably from about 7.2 to about 7.4.

In another aspect, the present invention provides an aqueous acid-concentrate composition useful in hemodialysis that contains, at a minimum, water, chloride, citrate, and cations to provide for a neutral (i.e., no net charge) composition, but does not contain any of bicarbonate, acetate or lactate. The water is "treated water" as defined herein, or a water of even greater purity, and each of the chloride and citrate is USP-grade quality or better (for example, reagent grade, preferably of at least 99% purity). In a related aspect, the aqueous acid-concentrate composition is prepared from water and a solid composition that, upon mixing with water, affords the aqueous acid-concentrate composition having the components described above. Thus, the present invention also provides, in one aspect, this solid composition.

The aqueous acid-concentrate composition contains chloride at a concentration of about 1,000 to about 7,000, preferably of from about 2,000 to about 5,000 mEq/L; citrate at a concentration ranging from about 20 to about 200, preferably from about 70 to about 150 mEq/L; and sufficient physiologically-acceptable cations to provide for a neutral (i.e., no net charge) composition, where the composition has a pH of less than 4, preferably between about 2 and about 3, and more preferably about 2.2 to 2.8, and does not contain any of bicarbonate, acetate, or lactate. The present invention also provides the same composition in a water-free form which, upon mixing with water, will form the aqueous acid-concentrate composition described above. The water-free form may be in the form of, e.g., a pellet, tablet or powder.

Although this aqueous acid-concentrate composition does not contain any of bicarbonate, acetate or lactate, it is still usefully employed in dialysate manufacture. For instance, it provides a convenient stock solution to which may be added bases and/or salts. Since it is a liquid, it is conveniently employed as the acid concentrate in traditional dialyzers that employ the three-stream proportionate pumping mechanism for making dialysate. Care should, however, be taken when combining base, such as bicarbonate, with the aqueous acid-concentrate composition, in order that the desired pH of the final dialysate is obtained.

In a related embodiment, the invention provides a method of preparing dialysate, wherein a basic solution containing water and at least one of bicarbonate, carbonate, acetate, lactate, and citrate having a pH of greater than 7 is mixed with the aqueous acid-concentrate composition described above, i.e., an acidic solution having a pH of less than 4 containing, at a minimum, chloride, citrate, and cations, the cations providing for an electronically neutral composition, where this acidic solution does not contain any of bicarbonate, acetate or lactate. According to this method, the relative amounts of basic and acidic solutions that are combined should be carefully tailored so as to achieve a desired dialysate pH, at all times throughout a dialysis treatment session. Typically, that desired dialysate pH is within the range of 6.8 to 7.8.

While citric acid-containing hemodialysate compositions are known in the art, see U.S. Pat. No. 5,252,213 of Ahmad et al., such compositions are disclosed as dry pellets (or other like solid form) which are dissolved in water to provide the hemodialysate composition. Those compositions provide a convenient source of all of the components of a hemodialysate composition, and are intended to be combined with water and essentially no other ingredients, before being used in a hemodialysis treatment. Thus, each pellet contains both the acidic and basic components of a hemodialysate composition which ensures the pH of the resulting hemodialysate.

The present invention makes an aqueous acid concentrate that may be used in the preparation of either hemodialysate or peritoneal dialysate. The citric acid concentrate is intended to be combined with treated water and base concentrate, as is currently the practice in dialysis clinics, so as to afford the dialysate composition. In clinics, the pH of the base concentrate, which typically contains sodium bicarbonate, can vary widely and affect the resulting dialysate pH. Therefore, when using a citric acid-containing acid concentrate in the manner according to the present invention, the concentrate should contain a buffering agent in order to maintain the resulting dialysate pH within a pre-determined, physiologically-acceptable range throughout the duration of the dialysis treatment. Buffering is required because increasing the amount of citric acid to lower the dialysate pH may cause a significant decrease in serum calcium concentration. This need for a buffer with citric acid concentrate is a departure from the practice in the art.

Most dialysates in use today use acetic acid as the acidifying agent to keep the pH of the final dialysate within an acceptable physiological range. As noted above, the 'acid concentrate' that is used in most hemodialysis treatments today is shipped as a liquid. The concentrate is in liquid form because acetic acid is a liquid acid. Although this solution is far more concentrated than the final dialysate which is actually used to purify a patient's blood (it can be as much as 45 times more concentrated), still three-quarters of its weight and volume is water. The present invention utilizes citric acid, rather than acetic acid, as the main acidic material in an acid concentrate.

In an acid concentrate that contains citrate, the citrate will be primarily in the form of citric acid. There are certain ramifications of using citric acid in an acid concentrate for dialysate. For example, citric acid forms citrate in the blood which binds with free magnesium and calcium. In fact, the strong binding of calcium with citrate is used by blood banks to prevent clotting in donated blood. While the level of citric acid used in the dialysate of the present invention is only a fraction (less than one-quarter) of the amount needed to achieve measurable anticoagulation, medical prudence dictates using the least amount of citric acid possible in a dialysate in order to minimize undesired calcium binding in the blood. When dialysate is prepared from 45× dilution of precursor dialysate, and the precursor dialysate has citrate concentrations within the range of 200-900 mEq/L, then the precursor preferably has elevated levels of calcium and/or magnesium to compensate for the extent to which citrate will bind serum calcium and magnesium.

The amount of citrate present in the acid concentrate of the invention should be the least amount necessary to achieve a final dialysate pH within the range of 7.2 to 7.4. We have found that using about 7 grams citric acid per liter of water in an acid concentrate (providing a concentration equal to 2.4 mEq/L) would minimize the calcium binding and achieve an acceptable dialysate pH.

However, the use of citrate in an acid concentrate led to an intermittent problem when the dialysate was used in a clinical setting. Generally, late in a dialysis session (usually in the last hour of treatment) some dialysis machines would sound an alarm due to high pH. This problem was traced to the base solution.

Bicarbonate is the basic material present in most base solutions. In most dialysis clinics, the bicarbonate solution is made by the clinic staff just before use. The procedure often can involve pouring a pre-determined amount of sodium bicarbonate (typically one package) into a jug, adding a measured amount of water and manually mixing (usually by shaking the container). Any, some, or all of the following factors may cause variations in the pH of the bicarbonate from the expected standard: the amount of water added can be more or less than specified, the mixing can be insufficient to thoroughly put all the sodium bicarbonate powder into solution, the container could be left sitting for a period before use, or the patient has a long dialysis treatment.

When carefully measuring and adequately mixing the bicarbonate, the pH of the concentrated solution was 7.85 (±0.05). However, in practice, samples of bicarbonate concentrate that are prepared by clinic staff had a range of pH values from 7.78 to 8.13. Furthermore, the pH of the residual bicarbonate concentrates that had just been used for a hemodialysis treatment were found to range from 7.9 to 8.24. We speculate that this variation in pH, most noticeably observed in the 'spent' dialysate, may be from any one of, or a combination of, the following factors:

Insufficient water was added to the base concentrate, causing a higher than desired concentration of bicarbonate.

Inadequate mixing of the powder and water, allowing some settling of the powder and therefore a more concentrated bicarbonate solution and rising pH late in the dialysis treatment (at which time the powder has completely dissolved).

The bicarbonate concentrate releases carbon dioxide over time, thereby causing slowly increasing pH.

One way to ensure against the pH rising to the alarm threshold during a dialysis treatment is to increase the amount of acid used, which causes a more acidic dialysate. However, increasing the amount of citric acid also increases the amount of calcium binding—accordingly, this approach must be used with caution. An alternative approach taken according to the present invention is to mitigate the effects of an increase in dialysate pH which is caused by a rising pH of the bicarbonate concentrate, through inclusion of a buffering agent in the acid concentrate.

Acetate and/or lactate were selected as the preferred buffering agents in the present invention. Each of these anions is found naturally in the blood of dialysis patients. Sodium acetate is a preferred buffer because it contains the same ingredients, sodium and acetate, that are in virtually all current dialysates (provided from the sodium chloride and acetic acid).

Surprisingly, there is not a linear relationship between the amount of sodium acetate buffer present in the acid concentrate and the pH of the final dialysate solution. It might be expected that adding increasing amounts of this acidic buffer to an acid concentrate would cause a linear decrease in the pH of the final solution. However, this is not the case. Within a narrow range the sodium acetate causes a significant decrease in the pH of the dialysate. However, this buffering action of the sodium acetate is only observed when the pH of the bicarbonate concentrate exceeds 8.0. At higher pH values of the bicarbonate concentrate, the buffering action of the acetate is more apparent.

Figure 1:
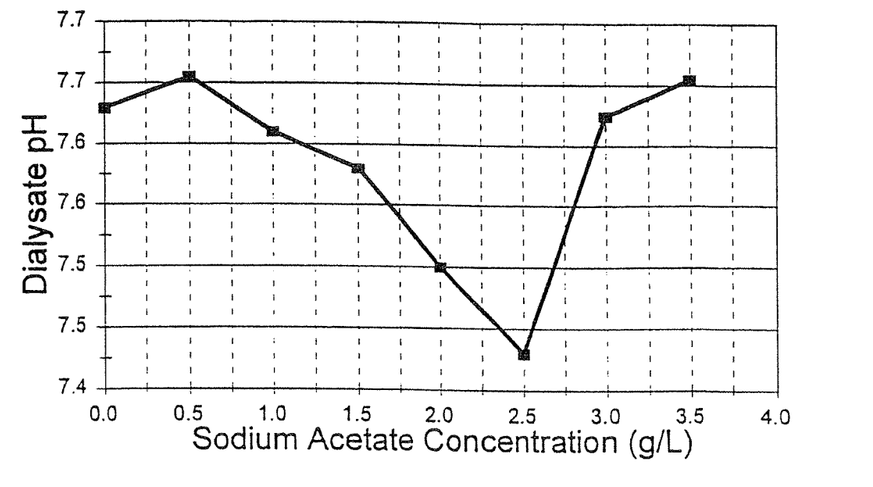
The FIGURE is a plot of Dialysate pH (y-axis) vs. Sodium Acetate Concentration (x-axis), and shows the effect on pH of adding sodium acetate to dialysate when the bicarbonate concentrate solution had an initial pH of 8.14.

This effect is shown in the FIGURE. The chart of the FIGURE illustrates the resulting dialysate pH obtaining using a relatively high bicarbonate concentration at pH 8.14 combined with treated water and the present invention's dialysate precursor using 2.4 mEq·L of citrate and increasing the sodium acetate concentration from 0 to 3.5 grams per liter. As shown in the FIGURE, increasing the concentration of sodium acetate beyond a certain point does not increase the sodium acetate's buffering action nor does it make the buffering action apparent at lower values of bicarbonate pH. While not wishing to be bound by theory, the following is suggested to explain the surprising effect of using acetate in the acid concentrates of the invention.

Citric acid is a multi-protic acid. It contains three labile hydrogen atoms that can contribute to the acidity of a solution. There is a separate equilibrium associated with the liberation of each hydrogen ion:

$$H_3A \leftrightarrow H^+ + H_2A^- \quad K_{a1} = 7.10 \times 10^{-4} \text{ at } 20°C. (pKa = 3.14)$$
$$H_2A^- \leftrightarrow H^+ + HA^{2-} \quad K_{a2} = 1.68 \times 10^{-5} \text{ at } 20°C. (pKa = 4.77)$$
$$HA^{2-} \leftrightarrow H^+ + A^{3-} \quad K_{a3} = 6.4 \times 10^{-6} \text{ at } 20°C. (pKa = 6.39)$$

where A represents the citrate anion. At a pH greater than 7 almost all of the citric acid is dissociated and the predominant species are $H^+$ and $A^{3-}$.

Acetic acid is a monoprotic acid, i.e., it contributes only one labile hydrogen atom to the solution and there is only one equilibrium constant for the equilibrium:

$$HAc \leftrightarrow H^+ + Ac^- \quad K_a = 1.76 \times 10^{-5} \text{ at } 25°C. (pKa = 4.75)$$

where Ac represents the acetate anion. When sodium acetate (NaAc) is introduced to aqueous solution it dissolves completely into sodium ions ($Na^+$) and acetate ions ($Ac^-$). The sodium is considered to be a 'spectator' ion—it does not participate in any equilibria. The acetate ($Ac^-$) anion undergoes hydrolysis:

$$Ac^- + H_2O \leftrightarrow HAc + OH^- \quad K_b = K_w/K_a = 10^{-14}/1.76 \times 10^{-5} = 5.6 \times 10^{-10}$$

A buffer is a solution whose composition is designed to resist changes in pH. Small amounts of acid or base can be added to a buffer and the pH will change very little. These statements imply that the buffer solutions are able to react with both $H^+$ (also commonly written as $H_3O^+$) and $OH^-$ ions. Two common kinds of buffer solutions are ones which contain (1) a weak acid plus a salt of the weak acid, and (2) a weak base and a salt of the weak base. A less common type contains a weak acid (e.g., citric acid) and a salt of another weak acid (e.g., sodium acetate which is derived from acetic acid).

For simple aqueous solutions, the buffering action can often be calculated based on available data, specifically: concentration of acid, concentration of salts, temperature, and appropriate equilibrium constants, $K_i$. The situation with the acid concentrates and dialysates of the present invention is more complex. Additional equilibria are introduced by the addition of calcium (Ca) and magnesium (Mg) to the dialysate. These metal ions have their own equilibria with carbonate, acetate, and citrate ions. Equilibrium constants $K_i$, for some of the equilibria are not available and so their impact on the pH of a dialysate formulation cannot be absolutely predicted. Direct measurement of solution pH by titrimetric methods may be used in the formulation of the dialysate. The predominant equilibria in solution are given by (not an exhaustive list):

$$H_3A \leftrightarrow H^+ + H_2A^- \quad K_{a1} = 7.10 \times 10^{-4} \text{ at } 20°C. (pKa = 3.14)$$
$$H_2A^- \leftrightarrow H^+ + HA^{2-} \quad K_{a2} = 1.68 \times 10^{-5} \text{ at } 20°C. (pKa = 4.77)$$
$$HA^{2-} \leftrightarrow H^+ + A^{3-} \quad K_{a3} = 6.4 \times 10^{-6} \text{ at } 20°C. (pKa = 6.39)$$

where A represents the citrate anion.

$$Ac^- + H_2O \leftrightarrow HAc + OH^- \quad K_b = K_w/K_a = 10^{-14}/1.76 \times 10^{-5} = 5.6 \times 10^{-10}$$

where Ac represents the acetate anion.

$$H_2O \leftrightarrow H^+ + OH^- \quad K_w = 10^{-14} \text{ at } 25°C. \text{ (Also written as } 2H_2O \leftrightarrow H_3O^+ + OH^-)$$
$$HCO_3^- \leftrightarrow H^+ + CO_3^-$$
$$Ca^{2+} + 2Ac^- \leftrightarrow CaAc_2 \quad K_{sp} = \text{solubility product constant, i.e., the solubility of calcium acetate}$$
$$Mg^{2+} + 2Ac^- \leftrightarrow MgAc_2 \quad K_{sp} = \text{solubility product constant, i.e., the solubility of magnesium acetate}$$
$$3Ca^{2+} + 2Ac^{3-} \leftrightarrow Ca_3A_2 \quad K_{sp} = \text{solubility product constant, i.e., the solubility of calcium citrate}$$
$$3Mg^{2+} + 2A^{3-} \leftrightarrow Mg_3A_2 \quad K_{sp} = \text{solubility product constant, i.e., the solubility of magnesium citrate}$$

Since the $A^{3-}$ species predominates at a pH above 7.0, the calcium and magnesium equilibria with lower citrate ions ($HA^{2-}$ and $H_2A^-$) are not considered.

$$Ca^{2+} + CO_3^{2-} \leftrightarrow CaCO_3 \quad K_{sp} = \text{solubility product constant, i.e., the solubility of calcium carbonate}$$
$$Mg^{2+} + CO_3^{2-} \leftrightarrow MgCO_3 \quad K_{sp} = \text{solubility product constant, i.e., the solubility of magnesium carbonate}$$

If all of the constants and concentrations were known for 37° C., then the above equations could be set into a matrix and the pH and buffering action could be obtained by calculation. The situation is further restrained by the requirement to keep the pH within a physiological range (especially near the end of dialysis when the pH of the bicarbonate concentrate tends to rise). Normally, this could be accomplished with the addition of more (citric) acid, however, this is precluded by the need to keep the concentration of citrate ions (from citric acid) as low as possible. As discussed below, this is required because of the tendency of calcium and magnesium to combine with citrate ions thus lowering the serum levels of calcium and magnesium to clinically unacceptable levels. The solution to this problem is found in Applicants' selection of the buffer.

Sodium citrate is not used in the buffer because of the aforementioned need to maintain an acceptably low total citrate ion concentration. Acetate or lactate may be used because of (1) their appropriate buffering action, (2) cost, (3) acetate ions (which are preferred) are already used (from acetic acid) in dialysate formulations and thus no new variable is introduced to the chemistry of the dialysate.

The buffering action manifests itself by lowering the pH of the dialysate to physiological, non-alarm levels when the pH of the bicarbonate is high—either from incorrect mixing or the passage of time since mixing. When the bicarbonate pH is appropriate, the buffer is present, but it is transparent to the operation of the dialysate. When bicarbonate concentrate solutions were used with a pH of <8.0 the buffering action was not apparent. When bicarbonate concentrate solutions of 8.1<pH<8.3 were used, the buffering action was evident (see FIGURE). The buffering action is particularly evident for sodium acetate concentrations between 0.5 and 3.0 g per liter of acid concentrate, where this is a preferred range for the acid concentrates of the present invention.

In another aspect, the present invention provides citrate-containing compositions particularly suitable for peritoneal dialysis (PD). These composition may be in either solid or liquid form, i.e., either a mixture of dry ingredients, which is a precursor to the peritoneal dialysate, or a solution of various solutes, which itself is a peritoneal dialysate. The mixture of dry ingredients contains, at a minimum, chloride, citrate, bicarbonate and dextrose, along with one or more cationic species that provide a neutral (i.e., no net charge) composition. The solution form of the PD composition contains, at a minimum, water in addition to the above-listed minimum ingredients required for the dry composition. Whether in solid or liquid form, the citrate acid-containing compositions suitable for peritoneal dialysis are sterile.

The peritoneal dialysate of the present invention (i.e., the PD solution dialysate) contains water in addition to the following ingredients, in the indicated amounts, where the amounts are expressed in terms of mEq per liter of the PD solution: citrate (0.5-6, preferably 1.5-4.5, more preferably 2-3); chloride (20-200, preferably 40-150, more preferably 60-120); and bicarbonate (5-100, preferably 10-70, more preferably 30-40). In addition, the solution form of the PD composition contains glucose at a concentration, in terms of g per liter of the solution form, of 10-100, preferably 20-80, more preferably 40-60. In addition, the solution form of the PD composition contains a sufficient number of physiologically-acceptable cations to neutralize all of the citrate, chloride, bicarbonate, and any other anionic species that may be present in the composition. This PD solution dialysate is sterile, as required for all dialysates approved for peritoneal dialysis by the U.S. Food & Drug Administration.

In a preferred embodiment, the solution form of the PD composition contains acetate and/or lactate, where in total these two anions are present in an amount, expressed in terms of mEq per liter of PD solution, of 0.01-10, preferably 0.1-1, more preferably 0.25-0.75. The cationic species present in the PD solution are essentially within the same concentration ranges as previously set forth herein for cationic species (i.e., sodium, magnesium, calcium and potassium) in the hemodialysis compositions.

The present invention provides a dry composition which, upon combination with sterile water, will generate the above-described PD solution dialysate. This dry composition is, itself, sterile. According to one approach, such a dry composition can be described in terms of grams of a specific ingredients per each (one) gram of citrate. Using these terms, the dry composition contains chloride in an amount of 5-50, preferably 10-40, more preferably 20-30; bicarbonate in an amount of 1-50; preferably 5-30, more preferably 10-20; and glucose in an amount of 100-600; preferably 150-500, more preferably 200-350, where each of these values are grams per 1 gram of citrate. In calculating these amounts, the formula weights for citrate, chloride, and bicarbonate are 189.1 g/mol, 35.5 g/mol and 61.0 g/mol, respectively, where each of chloride and bicarbonate carry a single charge, while citrate carries a triple charge. The dry PD composition contains sufficient cationic species to provide a neutral (no net charge) composition. In addition, the pH of the resulting solution will be within a physiologically tolerable range, preferably within the range 6.4-7.6.

According to another approach, the content of the dry PD composition can be described in terms of the number of milli-equivalents of a specific charged species present in the composition per each (one) milli-equivalent of citrate present in the composition. In these terms, the dry composition contains chloride in an amount ranging from 1-200, preferably 10-100, more preferably 30-50 mEq; and bicarbonate in an amount ranging from 1-50, preferably 5-30; more preferably 10-20 mEq. In addition, the dry PD composition contains glucose in an amount of 100-600; preferably 150-400, more preferably 200-300, where each of these values are grams per 1 gram of citrate.

Both the peritoneal dialysate and the dry precursor thereto are necessarily sterile in order to be useful in peritoneal dialysis. Accordingly, the preparation of each is necessarily conducted under sterile conditions, and/or the resulting composition is rendered sterile by appropriate sterilizing treatment. According to one embodiment, the dry PD composition is prepared by combining sodium chloride (5.67 g), calcium chloride dihydrate (0.26 g), magnesium chloride hexahydrate (0.10 g) sodium bicarbonate (2.94 g), anhydrous citric acid (0.15 g), sodium acetate trihydrate (0.041 g) and dextrose (42.5 g), where each of the listed chemicals is in sterile form, and the combining procedure is conducted in a sterile environment. This dry composition contains 0.15 g citrate, 3.6 g chloride, 2.1 g bicarbonate and 42.5 g glucose which, in terms of each gram of citrate, is 24 g chloride, 14 g bicarbonate and 283 g dextrose, and in terms of each milli-equivalent of citrate is 42 mEq chloride and 14.5 mEq bicarbonate.

The dry PD composition, and the peritoneal dialysate prepared therefrom, is described in terms of anionic species because each anionic species may be introduced into the composition in any dry form that is physiologically acceptable and contains the anionic species of interest. Thus, for example, "citrate" can be introduced into the dry composition in any dry form that contains citrate. Examples are citric acid (anhydrous), citric acid monohydrate, trisodium citrate, citric acid disodium salt sesquihydrate, citric acid monosodium salt, citric acid tripotassium salt monohydrate, etc. Likewise, each of the bicarbonate and chloride may be introduced simultaneous with cations selected from sodium, potassium, magnesium and calcium, and may be in anhydrous or hydrate forms. Accordingly, the dry composition is described in terms of "chloride", "citrate", and "bicarbonate", rather than specifying any particular salt or protonated form thereof.

The chloride is present in the dry composition in the form of a salt. Suitable chloride salts include, without limitation, sodium chloride, potassium chloride, calcium chloride, and magnesium chloride. A preferred chloride salt is sodium chloride.

The citrate is present in the dry composition in form of an acid and/or a salt. Citric acid is a suitable acid form of citrate. Trisodium citrate, tripotassium citrate, and calcium citrate (i.e., tricalcium dicitrate) are all suitable salt forms of citrate. The citrate may be in a mixed acid/salt form, i.e., complexed simultaneously to one or more protons and one or more metal cations. Typical examples of citrate in mixed acid/salt form include, without limitation, potassium dihydrogen citrate, dipotassium hydrogen citrate, and disodium hydrogen citrate. A preferred citrate is citric acid.

The bicarbonate is present in the dry composition in the form of a salt. Suitable bicarbonate salts include, without limitation, sodium bicarbonate, and potassium bicarbonate. A preferred bicarbonate salt is sodium bicarbonate.

Glucose is a component of most of the currently used peritoneal dialysates, and is incorporated into the peritoneal dialysate (and precursor thereto) of the present invention in order to provide the benefits that glucose is known to provide to peritoneal dialysates. For example, glucose is primarily useful as an osmotic agent, as discussed previously, and is also recognized to mitigate some of the undesirable side-effects of peritoneal dialysis. The glucose may also provide some nutritional supplement to the subject undergoing to the dialysis treatment. The most typical glucose isomer currently used in peritoneal dialysate is dextrose, i.e., α-D-glucose. This is a commonly known material of commerce, and is available in both hydrated and anhydrous forms. Either form may be used in the present PD composition.

Although the dry composition will be dry to the touch, it may contain some water. For instance, several of the salts and acids mentioned above as suitable ingredients for the dry PD composition are commonly available in hydrated form. Such hydrated forms are suitably used in preparing the dry PD composition provided herein. Each of the above-mentioned ingredients of the dry PD composition is available from many commercial supply houses. See, e.g., Sigma-Aldrich. Preferably, the ingredients are of United States Pharmacopeia (USP)-grade purity or higher, which is generally recognized as a purity of at least about 95%.

Optional ingredients may be present in the dry PD composition. Suitable optional ingredients include, without limitation, amino acids.

The dry PD composition is readily prepared simply by mixing together weighed quantities of the various dry sterile ingredients under sterile conditions. Mixing is readily accomplished by agitating a combination of the ingredients until a homogeneous mixture results. The pre-weighed dry mixture may be packaged in hermetically-sealed packages for convenience in shipping, and to allow a technician to more easily prepare a solution form of the dry composition.

The dry dialysate powder technology of the present invention allows the preparation of peritoneal dialysate. This aspect of the invention creates a unique peritoneal dialysate using, in a preferred embodiment, citric acid as the acidifier, dextrose at concentrations exceeding 2.0% and bicarbonate as the basic anion. Other ingredients would include water as well as chloride, sodium, potassium, magnesium, and calcium, which could all be included at the concentration ranges specified for hemodialysis dialysate. Peritoneal dialysate would require no precursor (other than the dry powder) since the volumes of dialysate used per treatment are just a small fraction of the amounts used in hemodialysis. Making the peritoneal dialysate just prior to use (i.e., by adding sterile water to the sterile dry PD powder) would allow the use of bicarbonate as the basic anion. Normally, bicarbonate cannot be used in PD because solutions of it with citric acid do not have sufficient long-term stability to permit storage. To overcome this stability problem, currently used PD compositions typically contain lactate (rather than bicarbonate) as the basic anion. However, some health care professions prefer bicarbonate as the basic anion, and the present invention addresses that need.

The precise order in which the sterile water and dry ingredients are combined is unimportant. As one option, sterile water may be added to the dry PD composition described above. As another option, a desired volume of sterile water may be provided, and to this may be added each of the various other (sterile) ingredients of the solution PD composition. Typically, the final solution should be stirred or otherwise agitated, e.g., shaken, to form a homogeneous composition. "Handbook of Dialysis" $2^{nd}$ Ed. Daugirdas, J. T. and Ing T. S., eds. (Little, Brown, Boston, 1994) provides an extensive discussion of peritoneal dialysis (as well as hemodialysis).

Physiological Effects

Citric acid was identified as a potential acidifying agent for dialysate because it is an inexpensive physiological acid. In addition, it has an extensive history of use in blood banks and also has been successfully used for regional anticoagulation in hemodialysis. Both these prior uses are based on the calcium binding effect of the citric acid. It is empirically observed that blood will coagulate if the concentration of free calcium in the blood is above a certain critical concentration. As citric acid is added to blood, the citrate binds with the free calcium and reduces its concentration. When the free calcium concentration is reduced to a certain point, the blood will no longer coagulate.

In the present invention, citric acid is employed in dialysate as an acidifying agent to reduce the pH of the dialysate. However, using more than about 2.4 mEq/L of citric acid in dialysate may possibly cause a decrease in serum calcium concentration, which may be clinically undesirable. At the level of 2.4 mEq/L of citric acid in dialysate, the increase in blood citrate concentration is typically small enough to not cause any noticeable detrimental effect on the coagulation behavior of blood. Indeed, there is typically no measurable increase in a patient's clotting time beyond that already achieved with their normal anticoagulation medicine, heparin.

Generally, kidney failure patients suffer from chronic acidosis. Their kidneys cannot rid the body of the H+ ions produced during normal metabolism. As a consequence, their bodies use excessive amounts of bicarbonate to buffer excess H+ ions. Because of the constant use of bicarbonate to neutralize acid, these patients have lower than normal levels of bicarbonate (carbon dioxide) when they arrive for their dialysis treatment. Traditionally, dialysis treatment seeks to correct an acidosis problem by using dialysate that contains higher than normal serum concentrations of bicarbonate. Thus, during treatment, the blood bicarbonate increases because of diffusion of some of this excess bicarbonate into the blood which helps restore total body bicarbonate. However, the traditional dialysis with a dialysate bicarbonate concentration of about 37 mEq/L is often not enough to maintain normal blood bicarbonate between dialysis sessions. Consequently, by the time the patient comes for the next dialysis session, the blood bicarbonate is again subnormal. The buffered citrate dialysate(s) of the present invention have shown some effect at replenishing the body's bicarbonate levels, thus helping to treat chronic acidosis.

The following examples are provided for purposes of illustration, not limitation.

EXAMPLES

Example 1

Acid Concentrate Formulation

The following amounts of the indicated USP-grade chemicals were carefully weighed out: 262.0 g sodium chloride (FW 58.45), 9.70 g calcium chloride (dihydrate, FW 147.02), 3.40 g magnesium chloride (hexahydrate, FW 203.3), 90.0 g dextrose (FW 180.16), 7.0 g citric acid (anhydrous, FW 192.12) and 1.75 g of sodium acetate (trihydrate, FW 136.08). The chemicals were placed in a large calibrated beaker and AAMI quality water was added to the 900 ml mark. The beaker was placed on a stirring plate and a stirring bar was used to agitated the chemicals and water. After approximately 10 minutes of stirring, the chemicals had completely dissolved and the solution was 'crystal clear.' The stirring bar was removed and the solution was 'topped off' with additional AAMI quality water to the 1 liter mark on the beaker. The stirring bar was reintroduced and the solution was stirred for another 3 minutes.

Example 2

Hemodialysis

The beaker of solution as prepared in Example 1 was taken to a Fresenius hemodialysis machine that was ready for use in testing (bypass) mode. In this configuration the machine makes dialysate in the same manner as when a patient is undergoing a dialysis treatment. The treated water supply line was attached to the machine and a container of bicarbonate concentrate was carefully prepared. All solutions were then attached to the machine and it was turned on.

The machine was allowed to run for 10 minutes at a dialysate flow rate of 800 ml/min. to ensure the prepared solutions had thoroughly filled their appropriate pathways through the machine. Additionally, both the machine's conductivity meter as well as an additional conductivity monitor that had been attached to the dialysate outflow line were monitored, with readings found to stay within the acceptable range (between 1310 and 1330 millisiemens). The pH of the machine-mixed dialysate was monitored by sampling the drain tube outflow at several intervals which averaged 10 minutes apart. The pH was 7.4, which was within the target range of 7.3 to 7.5. A sample of the outflow was analyzed at the University of Washington Medical Center's laboratory to confirm that the concentrations in the final dialysate were all within acceptable ranges for hemodialysis.

Finally, after receiving the appropriate approvals, the dialysate precursor and the resulting dialysate produced by the hemodialysis machine were repeatedly tested in actual patient treatments during clinical trials of the new dialysate. Throughout the trials, even with dialysis sessions lasting up to five hours, there were no instances of pH alarms noted.

Example 3

Dialysate Composition

One liter of dialysate composition, excluding sodium bicarbonate, in mEq/L, contains: sodium, 100.3; chloride, 104.25; calcium, 2.5; potassium, 1.0; magnesium, 0.75; acetate, 0.3; citric acid, 2.4; and, in g/l, dextrose, 2.0. The total chemical composition of this dialysate composition (which did not contain sodium bicarbonate) was (in grams): NaCl (5.822); $CaCl_2 2H_2O$ (0.139); KCl (0.074); $MgCl_2 6H_2O$ (0.036); $NaC_2H_3O_2$ (0.039); $C_6H_8O_7$ (0.155) and $C_6H_{12}O_6 H_2O$ (2).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An aqueous acid-concentrate composition comprising water, chloride at a concentration of about 1,000 to about 7,000 mEq/L; citrate at a concentration ranging from about 20 to about 200 mEq/L; and sufficient physiologically-acceptable cations comprising calcium to provide for an ionically neutral composition, where the composition has a pH of less than 4, and does not contain any of acetate, bicarbonate or lactate.

2. The aqueous acid-concentrate composition of claim 1 comprising water, chloride at a concentration of 2,000 to 5,000 mEq/L; citrate at a concentration ranging from 70 to 150 mEq/L; and sufficient physiologically-acceptable cations to provide for an ionically neutral composition, where the composition has a pH of between 2 and 3, and does not contain any of acetate, bicarbonate or lactate.

3. The aqueous acid-concentrate composition of claim 1 wherein the physiologically-acceptable cations comprise a combination of calcium and magnesium.

4. The aqueous acid-concentrate composition of claim 2 wherein the physiologically-acceptable cations comprise a combination of calcium and magnesium.

5. The aqueous acid-concentrate composition of claim 1 where the composition has a pH of between 2.2 and 2.8 and does not contain any of bicarbonate, acetate or lactate.

6. The aqueous acid-concentrate composition of claim 2 where the composition has a pH of between 2.2 and 2.8 and does not contain any of bicarbonate, acetate or lactate.

7. A method of preparing an aqueous dialysate composition comprising mixing the aqueous acid-concentrate composition of claim 1, claim 2, claim 3, claim 4, claim 5 or claim 6 with a basic solution containing water and bicarbonate and having a pH of greater than 7.

8. An aqueous dialysate composition prepared according to the method of claim 7 having a pH in the range of 6.8 to 7.8.

* * * * *